(12) United States Patent
Brooker

(10) Patent No.: US 7,795,311 B2
(45) Date of Patent: Sep. 14, 2010

(54) METHODS AND COMPOSITIONS FOR THE MANAGEMENT OF SOIL-BORNE FUNGAL DISEASES

(75) Inventor: Nancy L. Brooker, Pittsburg, KS (US)

(73) Assignee: Pittsburg State University, Pittsburg, KS (US)

( * ) Notice: Subject to any disclaimer, the term of this patent is extended or adjusted under 35 U.S.C. 154(b) by 307 days.

(21) Appl. No.: 11/872,488

(22) Filed: Oct. 15, 2007

(65) Prior Publication Data
US 2009/0099262 A1 Apr. 16, 2009

(51) Int. Cl.
*A61K 31/192* (2006.01)
*A01P 3/00* (2006.01)
*A01N 25/26* (2006.01)

(52) U.S. Cl. .................... 514/569; 504/100; 504/121

(58) Field of Classification Search .................... None
See application file for complete search history.

(56) References Cited

U.S. PATENT DOCUMENTS

| | | | |
|---|---|---|---|
| 3,070,623 A | 12/1962 | Gottfried et al. |
| 3,676,102 A | 7/1972 | Clark et al. |
| 5,527,760 A | 6/1996 | Rensing et al. |
| 5,770,587 A | 6/1998 | Basilo et al. |
| 5,849,956 A | 12/1998 | Koga et al. |
| 5,965,545 A | 10/1999 | Ben-Shalom et al. |
| 6,444,233 B1 | 9/2002 | Arntzen et al. |
| 6,482,770 B2 | 11/2002 | Dutcheshen et al. |
| 6,673,749 B1 | 1/2004 | Singh et al. |
| 6,689,398 B2 | 2/2004 | Haridas et al. |
| 6,743,752 B2 | 6/2004 | Dutcheshen |
| 6,746,696 B2 | 6/2004 | Arntzen et al. |
| 6,773,727 B1 | 8/2004 | Rojas et al. |
| 6,777,004 B1 | 8/2004 | Wahidullah et al. |
| 7,105,186 B2 | 9/2006 | Arntzen et al. |
| 7,217,844 B2 | 5/2007 | Beauparlant et al. |
| 7,230,139 B2 | 6/2007 | Lavallee et al. |
| 2004/0035162 A1 * | 2/2004 | Williams et al. ................ 71/28 |
| 2004/0156920 A1 | 8/2004 | Kane |
| 2004/0202637 A1 * | 10/2004 | Yoshioka et al. ........ 424/70.121 |

FOREIGN PATENT DOCUMENTS

| | | |
|---|---|---|
| EP | 0136006 | 4/1985 |
| JP | 2005314285 | 11/2005 |
| WO | 0182697 | 11/2001 |

OTHER PUBLICATIONS

Marshall et al. (Phytochemistry. 2001; 58: 423-428).*
Brooker et al. (Biochemical Society Transactions. 2000; 28 (6): 917-920).*
Wolters, B. "Saponine als pflanzliche Pilzabwehrstoffe". Planta. vol. 79, 1968, pp. 77-83, XP002504722, Berlin, Germany; p. 79; Table 1.
Brooker et al. "Field Assessment of Plant Derivative Compounds for Managing Fungal Soybean Diseases". Biochemical Society Transactions. vol. 28, No. 6, 2000, pp. 917-920, XP002504723, abstract; p. 919; table 1.
Brooker et al. "Field Assessment of Plant Derivative Compounds for Managing Fungal Soybean Diseases". Proceeding of the 16th International Plant Lipid Symposium. Budapest, Hungary. [Online] Jun. 2004, pp. 149-152; XP002504724, Budapest. Retrieved from the Internet: URL: http://www.mete.mtesz.hu/pls/proceedings/index.htm [retrieved on Nov. 18, 2008] p. 149, paragraphs 2, 3; p. 150; Table 1.

* cited by examiner

*Primary Examiner*—Shanon A Foley
(74) *Attorney, Agent, or Firm*—Head, Johnson & Kachigian, P.C.

(57) ABSTRACT

Improved methods and compositions for protecting plants or seeds from soil-borne fungal diseases. The composition may include a triterpenoid isolated from *Glycyrrhiza glabra* and a polymer. The triterpenoid may be Carbenoxolone disodium salt, and the polymer may be a water-insoluble, water-soluble or flowable, seed coating polymer. The methods may comprise the steps of applying the composition to the plant's seeds, roots, tubers and/or foliage, and may also include applying the composition to the soil surround surrounding the plant. The composition may be applied as an aqueous solution or as dry particulates, and may be used for the treatment of soybean plants and seeds.

17 Claims, 9 Drawing Sheets

FIGURE 1

| 1999 Foliar Treatment Viability and Mortality Data |||| 
|---|---|---|---|
| Treatment | Total Morality/ Treatment | Mortality Percentage | Viability Percentage |
| Untreated Control | 388 | 20.2 | 79.8 |
| Magnacoat ® Only Control | 315 | 16.4 | 83.6 |
| Carbenoxolone (1000 µg/ml) | 388 | 20.2 | 79.8 |
| Carbenoxolone (500 µg/ml) | 315 | 16.4 | 83.6 |
| Carbenoxolone (250 µg/ml) | 269 | 14.0 | 86.0 |
| Carbenoxolone (125 µg/ml) | 200 | 10.4 | 89.6 |

FIGURE 2

| 1999 Mean Disease Rating for Each Foliar Treatment, Percent Mortality and the Statistical Significance ||||
|---|---|---|---|
| Treatment | Disease Rating | % Mortality | SNK |
| Control | 2.8 | 69 | A |
| Carbenoxolone (500 µg/ml) | 1.7 | 26 | B |
| Carbenoxolone (1000 µg/ml) | 1.7 | 22 | B |

FIGURE 3

| 2000 Foliar Treatment Viability and Mortality Data |||| 
|---|---|---|---|
| Treatment | Total Morality/ Treatment | Mortality Percentage | Viability Percentage |
| Untreated Control | 344 | 23.9 | 76.1 |
| Magnacoat ® Only Control | 286 | 19.9 | 80.1 |
| Carbenoxolone (1000 μg/ml) | 127 | 08.8 | 91.2 |
| Carbenoxolone (500 μg/ml) | 250 | 17.4 | 82.6 |
| Carbenoxolone (250 μg/ml) | 217 | 15.1 | 84.9 |
| Carbenoxolone (125 μg/ml) | 251 | 17.4 | 82.6 |

FIGURE 4

| 2000 Mean Disease Rating for Each Foliar Treatment, Percent Mortality and the Statistical Significance | | | |
|---|---|---|---|
| Treatment | Disease Rating | % Mortality | SNK |
| Control | 2.8 | 69 | A |
| Carbenoxolone (500 µg/ml) | 1.7 | 26 | B |
| Carbenoxolone (1000 µg/ml) | 1.7 | 22 | B |

FIGURE 5

| Comparison of Mean Soybean Pre-emergence Mortality and Standard Deviation According to Seed Treatment (n=4) | | | |
|---|---|---|---|
| | 2003 | 2004 | 2005 |
| Treatments | Mean Percentage | Mean Percentage | Mean Percentage |
| Untreated Control | 76±16.59 31.66% | 92 ± 9.90 38.33% | 57 ± 3.30 23.75% |
| Polymer Only | 89±12.11 37.08 5 | 100 ± 7.82 41.66% | 68 ± 7.37 28.33% |
| Carbenoxolone Seed | 63 ± 20.22 26.25% | 104 ± 8.44 43.33% | 70 ± 8.51 29.16% |
| Carbenoxolone R1 Foliar | 66 ± 17.85 27.50% | 99 ± 12.20 41.25% | 65 ± 5.86 27.08% |
| Carbenoxolone R4 Foliar | 85 ± 5.80 35.41% | 105 ± 16.35 43.75% | 67 ± 6.09 27.91% |
| Carbenoxolone Seed and R1 Foliar | 72 ± 14.59 30.00% | 99 ± 9.46 41.25% | 72 ± 8.05 30.0% |
| Carbenoxolone Seed and R4 Foliar | 88 ± 7.98 36.66% | 102 ± 9.67 42.50% | 69 ± 5.86 28.75% |

FIGURE 6

| Comparison of Mean Soybean Post-Emergence Mortality and Standard Deviation According to Seed Treatment ($n=4$) | | | |
|---|---|---|---|
| | 2003 | 2004 | 2005 |
| Treatments | Mean Percentage | Mean Percentage | Mean Percentage |
| Untreated Control | 9 ± 3.29<br>3.75% | 3 ± 0.63<br>1.25% | 6 ± 1.93<br>2.50% |
| Polymer Only | 11 ± 3.75<br>4.58% | 3 ± 0.63<br>1.25% | 8 ± 3.33<br>3.33% |
| Carbenoxolone Seed | 12 ± 6.34<br>5.00% | 5 ± 1.70<br>1.25% | 6 ± 2.78<br>2.50% |
| Carbenoxolone R1 Foliar | 12 ± 0<br>5.00% | 4 ± 2.29<br>1.60% | 8 ± 3.01<br>3.33% |
| Carbenoxolone R4 Foliar | 15 ± 4.98<br>6.25% | 4 ± 0.65<br>1.60% | 8 ± 2.06<br>3.33% |
| Carbenoxolone Seed and R1 Foliar | 13 ± 3.97<br>5.41% | 4 ± 2.36<br>1.60% | 8 ± 2.59<br>3.33% |
| Carbenoxolone Seed and R4 Foliar | 7 ± 1.32<br>2.90% | 5 ± 1.30<br>2.08% | 6 ± 3.38<br>2.50% |

FIGURE 7

| Comparison of Mean Soybean Viability and Standard Deviation According to Seed Treatments (n=4) | | | |
|---|---|---|---|
| | 2003 | 2004 | 2005 |
| Treatments | Mean Percentage | Mean Percentage | Mean Percentage |
| Untreated Control | 175 ± 16.59 72.91% | 159 ± 9.90 66.25% | 194 ± 3.30 80.83% |
| Polymer Only | 163 ± 12.11 67.91% | 151±7.82 62.91% | 183±7.37 76.25% |
| Carbenoxolone Seed | 188 ± 20.22 78.33% | 148 ± 8.44 61.66% | 181 ± 8.51 75.41% |
| Carbenoxolone R1 Foliar | 185±17.85 77.08% | 152 ± 12.20 63.33% | 186 ± 5.86 77.50% |
| Carbenoxolone R4 Foliar | 166 ± 5.8 69.16% | 146 ± 16.35 60.83% | 184 ± 6.09 76.66% |
| Carbenoxolone Seed and R1 Foliar | 179 ± 14.59 74.58% | 153 ± 9.46 63.73% | 179 ± 8.05 74.58% |
| Carbenoxolone Seed and R4 Foliar | 167 ± 12.34 69.58% | 149 ± 9.67 62.08% | 182 ± 5.86 75.83% |

FIGURE 8

| Student-Newman-Keuls Multiple Comparison of Mean *Phytophthora spp.* Within the Soil During the Developmental Stage R1 of Year 2004 Stage According to Seed Treatments (*n=4*) ||
|---|---|
| Treatments | Mean  SNK Rank |
| Untreated Control | 7.833   *BC* |
| Magnacoat® | 11.750   *ABC* |
| Carbenoxolone Seed | 17.000   *ABC* |
| Carbenoxolone R1 Foliar | 13.667   *ABC* |
| Carbenoxolone R4 Foliar | 8.583   *BC* |
| Carbenoxolone Seed and R1 Foliar | 16.750   *ABC* |
| Carbenoxolone Seed and R4 Foliar | 16.471   *ABC* |

FIGURE 9

| Student-Newman-Keuls Multiple Comparison of Mean Yield Bushels Per Acre for Years 2003, 2004, and 2005 Stage According to Seed Treatments (n=4) ||
|---|---|
| Treatments | Mean   SNK Rank |
| Untreated Control | 23.390   *A* |
| Magnacoat® | 23.064   *A* |
| Carbenoxolone Seed | 23.044   *A* |
| Carbenoxolone R1 Foliar | 23.548   *A* |
| Carbenoxolone R4 Foliar | 22.619   *A* |
| Carbenoxolone Seed and R1 Foliar | 24.686   *A* |
| Carbenoxolone Seed and R4 Foliar | 22.769   *A* |

METHODS AND COMPOSITIONS FOR THE MANAGEMENT OF SOIL-BORNE FUNGAL DISEASES

BACKGROUND OF THE INVENTION

1. Field of the Invention

The methods and compositions disclosed herein are broadly concerned with protecting plants or seeds from soil-borne fungal diseases. The composition may include a triterpenoid isolated from *Glycyrrhiza glabra* and a polymer. The triterpenoid may be Carbenoxolone disodium salt. The polymer coating decreases the miscibility of the Carbenoxolone disodium salt. The methods may include applying the composition to the plant's seeds, roots, tubers and/or foliage. The methods may also include applying the composition to the soil surround surrounding the plant. The composition may be applied as an aqueous solution or as dry particulates, and may be used for the treatment of soybean plants and seeds.

2. Prior Art

The soybean (*Glycine max*) is of worldwide significance both economically and agriculturally. Today, soybeans are grown in more than twenty-nine (29) states. Currently, the United States is the leading world producer of soybeans, accounting for nearly 2½ billion bushels per year. Animal feed accounts for nearly 75% of all domestic soybean meal consumption each year. Soybeans are also the foremost provider of protein and oil. A sixty (60) pound bushel of soybeans yields about forty-eight (48) pounds of protein-rich meal and eleven (11) pounds of oil. Products from soybeans include: tofu, soy milk, soy sauce, plywood, plastics, particle board, printing inks, soap, candy products, cosmetics and antibiotics, thus making soybeans a very economically important and diverse crop.

In 2005, the United States Department of Agriculture's National Agricultural Statistics Service ("NASS") reported production of 3.09 billion bushels of soybeans, with an estimated record high average yield of 43.3 bushels per acre. Despite this encouraging yield data, disease is still problematic to soybean farmers and results in loss of yield. In 2004, the University of Missouri-Delta Center reported that disease resulted in up to 485,000,000 bushels lost, approximately 2.4 billion dollars, in the United States. Furthermore, the incidence of *Macrophomina phaseolina* accounted for the loss of 10,849,000 of those bushels, at approximately 54 million dollars, while *Phytophthora* rot accounted for the loss of 57,116,000 bushels, at approximately 285 million dollars.

Soil-borne fungal diseases represent some of the most difficult diseases to control and manage due to their persistence, virulence and longevity. Reliance upon chemically synthesized pesticides in agriculture has resulted in a number of social and ecological problems, and a number of these pesticides are under evaluation by Federal agencies to assess their safety and environmental impact. With the strong public interest and Federal mandates to develop safer pesticides for the environment, there is strong support in the development of seed treatments to help manage these plant diseases. An alternate approach to controlling plant diseases is the use of natural products, specifically plant-derived compounds.

*Macrophomina phaseolina* ("Charcoal rot"), *Phytophthora* spp. ("*Phytophthora* rot"), *Pythium* spp., *Phoma* spp. and *Rhizoctonia solani* are some of the most prevalent and destructive soil-borne diseases in the Midwest. Due to pathogen persistence in over-wintering periods, as well as predictable environmental stresses on the plants, repeated planting of soybeans in a field increases the risk of infection. Due to this complexity in host-pathogen interactions, disease is difficult to control.

Although there are many available varieties of soybeans, no such cultivar exists that is genetically or otherwise resistant to all of these soil-borne diseases. Furthermore, no single fungicide has been developed to effectively control these pathogens under all environmental conditions. Specific methods explored for controlling disease include commercial fungicides, crop rotation, and regulated irrigation, though none of these have proven to be completely effective.

The host range of *Phytophthora* spp. is a very diverse, with *Phytophthora infestans* being one of the most infamous of the genus and is the cause of potato late blight, the causal agent of the Irish Potato Famine which destroyed crops in many areas of Europe in the 1840's. Potato late blight has been classified as one of most devastating pathogen events in human history. *Phytophthora sojae*, the cause of *Phytophthora* root rot of soybeans, was first described over forty (40) years ago, but remains epidemic and a problem for soybean producers worldwide. Infections of *Phytophthora* spp. causes symptoms including pre- and post-emergence damping-off, stem and trunk cancer, root and tuber rot, wilting and leaf blight. *Phytophthora* rot can attack plants at any stage of development. In young plants, symptoms include yellowing, wilting and collapse/rot of the root and vascular system. In mature plants, symptoms vary and include reduced vigor, yellowing of the leaves, discoloration of the stem, and wilting and death.

*Phytophthora* disease incidence is most common is poorly drained, clay soils, but can occur in well-drained, lighter soils if saturated for an extended period of time. Development of root rot in well drained, saturated soils is usually coupled with immature, developing plants having little defense. Other factors that affect crop losses are cultivar susceptibility, rainfall, soil type and soil compaction. Drip irrigation, used to supplement natural rainfall, increases the likelihood of disease development in crops that require additional water.

Common methods for controlling *Phytophthora* rot include race specific cultivars, improved drainage and tillage methods, chemical control to protect young emergent plants, antifungal seed treatments and crop rotation. Race-specific resistance is effective against certain races of the pathogen, but not all species. Improved drainage and tillage efforts have also been explored for further control of the spread and severity of *Phytophthora* rot. In most cases, conventional tillage practices bury surface residues and loosen surface and soil layers. Reduced till and no-till practices leave crop residue on the soil surface for decomposition. Another method to reduce disease severity is the use of seed or foliar compounds that provide antifungal activity. Chemical antifungal agents available are BSR-101, Corsoy 79 and Ridomil, which have shown to reduce the severity of *Phytophthora* when used in combination.

Foliar applications of Zoxamide have been shown to protect against *Phytophthora infestans.* Combination antifungal treatments Zoxamide plus mancozed resulted in lower levels of tuber infection, compared to previous individual treatments with chlorthalonil (Bravo), azoxystrobin (Quadris™), or manozeb (Dithane™). Phosphite foliar sprays have also been used to prevent infection by wind driven zoospores with treated plants showing significantly lower leaf and petiole symptoms than untreated plants. In soybeans, methods for control include variety selection, metalaxyl (Ridomil™) (N-(2.6-dimethylphenyl)-N-(methoxyacetyl)-DL-alanine methyl ester), metalaxyl (Allegiance™, Gustafons), mefenoxam (Apron XL™, Syngenta) fungicide use and potash fertilizer. These compounds have been shown to reduce the severity of *Phytophthora* root rot when used in combination with variety selection or resistant cultivars. However, species of *Phytophthora* have shown resistance to metalaxyl, especially *P. erythroseptica, P. citricola, P. nicotinanea* and *P. parasitica*.

*Macrophomina phaseolina* has been termed Charcoal rot due to the numerous black sclerotia produced during the pathogen's proliferate stage of growth in preparation for overwintering. Charcoal rot ranks high among economically important pathogens for soybean disease, following soybean cyst nematode, *Phytophthora* rot, and seedling disease. *M. phaseolina* has been known to cause seedling blight, Charcoal rot and root rot in at least five hundred (500) different plant species.

Charcoal rot infection is soil-borne and/or seed-borne and remains dormant until seeds germinate. It has been shown that more than 60% of developing colonies originate from sclerotia; concurrently, seedling emergence can be reduced by as much as 60% from planting already infected seeds. The symptoms of Charcoal rot become apparent during times of midsummer, hot, dry weather. The ability of the pathogen to cause disease is based on many factors, including the potential of the inoculum to cause disease, soil moisture, temperature, seed quality, seed density and level of propagules present. In post-emergence disease development, damping-off or wilting is the most common symptom. Later season symptoms occur during reproduction, and include, smaller or dwarf leaflets, yellowing or wilting of leaflets due to early senescence, reddish or brown discoloration of the pith of the tap root and black streaks in crown tissue. The most common diagnostic symptoms are sloughing off of cortical tissue, silvery-gray speckled appearance of the infected tissue and wilting of the crown of the plant, known as a "Shepherd's crook." All these symptoms are all due to the presence of sclerotia in the plant's vascular system. Seed yield is also reduced under these infection conditions.

Many cultural practices have been developed to manage the effects of Charcoal rot, and methods employed to reduce plant damage and increase overall plant health include decreasing seedling densities, planting later-maturity group cultivars, increasing soil fertility or crop rotation with less susceptible hosts. Additional methods investigated for improving plant health include biological control methods or hyperparasites, irrigation, fumigation of infested fields and the use of genetic resistant/tolerant cultivars.

Management strategies for controlling disease that include crop rotation and fall plowing to reduce inoculum densities in soil have been shown to be of limited benefit due to the wide host range of Charcoal rot. Soil populations of sclerotia seem to be reduced as soybeans are grown less frequently in crop rotation, even though other crops are susceptible. Furthermore, no fully resistant soybean germplasm exists, so improvement in disease resistant soybean cultivars has been limited. Many commercial and experimental plant varieties have been explored for resistance to *M. phaseolina*, and these cultivars do not show direct resistance to Charcoal rot infection, but they do seem to limit the growth rate of the fungus within the host. Additionally, lower plant populations or planting density have been explored to lessen the severity of Charcoal rot. This method is employed to promote rapid and strengthened growth and growth patterns, which proves beneficial in conjunction with mid-season irrigation and limited soil moisture. Water management and irrigation alleviate mid-season drought stress, and can limit, but not prevent colonization, of soybeans by sclerotia.

Tillage relationships with disease development have also been explored, but colonization of soybean roots occurred regardless of the tillage method used. Different soybean maturity groups and later planting dates have also been explored for disease control and resulted in later season flowering during times when the temperatures are lower and soil moisture is higher. However, varying planting dates can lead to problems with other pathogens, like later maturing soybean groups showing resistance to common pathogens, including the soybean cyst nematode, *Heterodera glycines*. Soil fumigation methods used to control pathogen populations in the soil prior to planting are of little benefit because the pathogen is found in both the seed and in the soil. Additional control methods explored include regulating such factors as soil moisture, temperature and nutrient levels to inhibit germination or growth of Charcoal rot.

With these disease management challenges, development of biological and natural control methods for *M. phaseolina* is an important avenue for exploration. By utilizing already present natural compounds and microbial parasites, there is less need for chemical fungicides and other synthetic chemical control measures. Bacterial parasites or sclerotial parasites have shown a reduction in germination of sclerotia. Natural plant-derived compounds have also been explored as alternatives for fungal disease management. Plant compounds such as lipids and lipid derivatives have also been shown to inhibit fungal growth in vitro, and in field trials, both as seed or foliar treatments.

General concern surrounds the uses of chemical pesticides in the United States because of possible environmental or human safety issues. Development of natural compounds for the control of disease and pests is of great interest. Natural plant derived compounds have been under investigation as possible control agents for some time.

Terpenoids and essential oils are secondary metabolites of plants. Carbenoxolone disodium salt is a terpenoid isolated from Licorice Root (*Glycyrrhiza glabra*) and a synthetic derivative from glycyrrhizinic acid. Carbenoxolone has anti-inflammatory properties and a noted binding affinity for albumin. Terpenoids disrupt the cell membrane's lipophilic compounds and are synthesized from acetate units and originate from the same compounds as fatty acids. Many uses of terpenoids have been described for the control of human diseases. Terpenoids from plants, like basil, have been shown to inhibit *Salmonella*, while others like betulinic acid have been shown to inhibit HIV.

Thus, there exists a need for a cost-effective, environmentally friendly composition and methods for effectively treating and/or preventing diseases in plants and seeds.

BRIEF DESCRIPTION OF THE DRAWINGS

FIG. 1 is a table illustrating 1999 Foliar Treatment Viability and Mortality Data;

FIG. 2 is a table illustrating 1999 Mean Disease Rating for Each Foliar Treatment, Percent Mortality and the Statistical Difference;

FIG. 3 is a table illustrating 2000 Foliar Treatment Viability and Mortality Data;

FIG. 4 is a table illustrating 2000 Mean Disease Rating for Each Foliar Treatment, Percent Mortality and the Statistical Difference;

FIG. 5 is a table illustrating a comparison of mean soybean pre-emergence mortality and standard deviation according to seed treatment;

FIG. 6 is a table illustrating a comparison of mean soybean post-emergence mortality and standard deviation according to seed treatment;

FIG. 7 is a table illustrating a comparison of mean soybean viability and standard deviation according to seed treatment;

FIG. 8 is a table illustrating Student-Newman-Keuls multiple comparison of mean *Phytophthora* spp. within the soil during developmental stage R1 of 2004 according to seed treatment; and FIG. 9 is a table illustrating Student-Newman-Keuls multiple comparison of mean yield of bushels per acre for years 2003, 2004 and 2005 according to seed treatment.

SUMMARY OF THE INVENTION

In general, the invention features a method of protecting a plant or seed from soil-borne fungal disease by applying an amount of a composition having a triterpenoid derived from *Glycyrrhiza glabra* and a polymer to a portion of the plant or seed to reduce or prevent the occurrence of fungal disease. The triterpenoid may be Carbenoxolone disodium salt (3β-hydroxy-11-oxoolean-12-en-30-oic acid 3-hemisuccinate disodium ($C_{34}H_{48}O_7Na_2$) (Formula Weight 614.72)). The polymer may be a water-insoluble, water-soluble or a flowable seed coating polymer. A flowable polymer may be water-soluble polymer whose solubility is less than the Carbenoxolone disodium salt in order to minimize loss of Carbenoxolone. The polymer may be a polyethar resin. The method may further include applying the composition to the plant as a foliar spray, applying the composition to a tuber of the plant, applying the composition to a portion of the roots of the plant or coating the seed with the composition. The composition may be an aqueous solution or may be dry particulates.

The fungal diseases treated according to the method using the composition may be *Acremonium* spp., *Alternaria* spp., *Arkoola nigra*, *Cercospora kikuchii*, *Cercospora sojina*, *Choanephora infundibulifera*, *Choanephora trispora*, *Colletotrichum dematium f. truncatum*, *Colletotrichum truncatum*, *Corynespora cassiicola*, *Cylindrocladium crotalarie*, *Dactuliochaeta glycines*, *Diaporthe phaseolorum*, *Diaporthe phaseolorum* var. *caulivora*, *Drechslera glycines*, *Fusarium solani f.* sp. *glycines*, *Glomerella glycines*, *Leptosphaerulina trifolii*, *Macrophomina phaseolina*, *Meocosmospora vasinfecta*, *Microsphaera diffusa*, *Mycoleptodiscus terrestris*, *Peronospora manshurica*, *Phakopsora pachyrhizi*, *Philophora gregata*, *Phoma* spp., *Phomopsis* spp., *Phyllosticta sojaecola*, *Phymatotrichopsis omnivora*, *Phytophthora* spp., *Pyrenochaeta glycines*, *Pythium* spp., *Rhizoctonia* spp., *Sclerotium rolfsii*, *Sclerotinia sclerotiorum*, *Septoria glycines*, *Spaceloma glycines*, *Stemphylium botryosum*, and *Thielaviopsis basicola*. The fungal disease *Phytophthora* spp. may be *Phytophthora sojae*. The fungal disease *Pythium* spp. may be *Pythium aphanidermatum*, *Pythium debaryanum*, *Pythium irregulars*, *Pythium myriotylum* or *Pythium ultimum*. The fungal disease *Rhizoctonia* spp. may be *Rhizoctonia solani*. The method and composition may be used to treat a soybean plants or seeds.

Plants treated according to and with the methods and compositions disclosed herein, or plants grown from seeds treated according to or with the methods and compositions, have exhibited reduced levels of fungal disease compared to untreated plants or seeds, and remain essential free of disease symptoms during development of the plants and seeds through the growing season.

DETAILED DESCRIPTION OF THE PREFERRED EMBODIMENTS

The methods and compositions discussed herein are merely illustrative of specific manners in which to make and use the invention and are not to be interpreted as limiting in scope.

While the methods and compositions have been described with a certain degree of particularity, it is to be noted that many modifications may be made in the details of the methods and compositions construction and the arrangement of their components without departing from the spirit and scope of this disclosure. It is understood that the methods and compositions are not limited to the embodiments set forth herein for purposes of exemplification.

As used herein, "plant" is intended to refer to any part of a plant, e.g., roots, foliage, shoots, stems, as well as tree, shrubbery flowers and grasses. "Seed" is intended to include seeds, tubers, tuber pieces, bulbs, etc., or parts thereof from which a plant is grown.

The time required for plant emergence depends on planting depth, vigor, soil moisture, soil temperature and plant variety. Developmental stages are identified after emergence. Vegetative growth is indicated by emergence of cotyledons and ends with the first flower. The VE stage is cotyledons or fleshy seed leaves above the soil surface, followed by VC, which is shown by cotyledons fully unfolded and the simple, or primary flag leaves have unfolded. The vegetative stages designated as (V1, V2, V3 and V(n)), wherein Vn equals the last node on the main stem at the time of first flower (n equals the number of nodes on the main stem with fully developed trifoliate true leaves beginning with the unifoliate node, i.e., V1). The reproductive stages begin with the first bloom or flower and ends at maturity and plant senescence. These are represented by four phases, flowering (R1 and R2), pod development (R3 and R4), seed growth (R5 and R6), and seed/plant maturation (R7 and R8).

Test plots were organized into randomized block design consisting of fifteen (15) total treatments. Treatments included either a control group, a seed treatment, foliar treatment, or a combination seed and foliar treatment. Each treatment consisted of four (4), twenty-five (25) foot rows in each test plot. The fifteen (15) treatment blocks were planted in quadruplicate for a total of sixty (60) test plots. The test plots were labeled with numerical identification markers which represent the treatment, plot, and replication number. No samples were taken from the two (2) interior rows of each plot so that they could be used for counting plant mortality and harvested for seed yields. The two (2) outside rows were used to sample plants.

Germination data was collected before each planting year. In 2003, 2004 and 2005, one-hundred (100) seeds were germinated to indicate rate of germination in laboratory conditions. In 2003 and 2005, the rate of seed germination was 95% and in 2004, the rate of seed germination was 96%. Test plots consisted of four (4) rows were based on eight (8) viable seeds per twenty-five (25) foot row. Ten (10) individual samples of two-hundred and forty (240) viable seeds were counted and weighed to estimate the seed weights per row. Each row was weighed in a Fisher® weigh boat, removing any damaged or non-viable seed and stacked in groups of four (4). The four (4) grouped weigh boats representing a single treatment plot. Upon planting two-hundred and forty (240) seeds in thirty (30) foot rows, the rows were end trimmed at two (2) weeks post-planting to twenty-five (25) foot row lengths.

Control treatment or treatments that did not include seed treatments were placed in labeled manila twenty pound (20 lb), 4×6 inch coin envelops and put in planting order based on a randomized plot design.

Seeds were treated with stock solutions of the following treatments. Carbenoxolone disodium salt 0, 125, 250, 500 and 1000 µg/L High Grade was utilized for management of *Pythium, Phytophthora, Phomopsis* and *Rhizoctonia* fungal pathogens. Gustafson's Magnacoat® (Gustafson, LLC, Plans, Tex.) was used as a seed-coating polymer in conjunction with the other treatment and as a control treatment. For example, stock solutions were prepared in 500 mL beakers as follows: Carbenoxolone1000 g/L High Grade was prepared by adding 0.105 g of 99% pure Carbenoxolone to 65 mL deionized water and mixing using a spatula until completely dissolved, then adding 35 mL Magnacoat® and 5 mL green Pro-Ized® colorant and mixing until homogenous for a total of 105 mL.

Seeds for each row were treated separately with compounds. A 2.1 mL sample was taken from the stock solution via pipette and placed in a 200 mL glass beaker. A single row seed sample was added to the beaker and the seeds were mixed with a glass stir rod until the seeds were completely covered. The samples were then spread onto a wax sheet and allowed to dry for one (1) to two (2) hours. Each treated seed sample was placed in a labeled twenty pound (20 lb), 4×6 inch manila coin envelope.

Foliar treatments were prepared on site. R1 and R4 Foliar Carbenoxolone 1000µ/mL treatments were prepared by adding 3.785 g Carbenoxolone to 1 gallon of water and mixed until dissolved. The mixture was then sprayed directly onto foliage using specialized $CO_2$ pressurized aerosol spray equipment set at a spray rate of 1 gallon/100 ft for four (4), twenty-five (25) foot rows and two (2) rows wide.

Germination data was taken at V1 by counting the emergent plants in the two (2) inner yield rows. Plant counts were used to compare with number of seeds planted to determine pre-emergence mortality due to soil-borne early season disease pressure. At the end of the growing season at developmental stage R7 when plants were mature, but before full senescence, dead plants were counted. Plant counts were used to determine mortality data for the season caused by overall disease pressure.

Plant height data was taken at each sampling stage; V1, R1, and R4. A height sample was taken from one (1) of the four (4) rows. The height was recorded from the base of the plant (at the soil line) to the top of the plant (terminal leaf node).

Beginning at developmental stage V1, a visual disease rating was employed to determine the overall visual health of the plant based on foliar, pod and stem disease. The foliar disease rating system was based from the Soybean Diseases Atlas by the Southern Soybean Disease Workers (W. J. Walla, ed. 1979, Texas A&M University). A 1-5 rating system was utilized, wherein 1=0%, 2=25%, 3=50%, 4=75%, 5=100% based on leaf area affected by disease symptoms.

Twenty random baseline soil samples were taken throughout the field previous to planting. Additional field soil samples were taken at four (4) different developmental stages; V1, R1, R4 and R6. Soil cores were taken between the first and second row of every plot in a designated one (1) square foot area. The samples were then placed in labeled Whirl-Pak® bags (Nasco Corporation), and returned to the lab for processing. Soil samples were then air dried and stored at room temperature until processing. Plant samples were also collected at the same developmental stage: V1, R1, R4, and R6; two (2) samples were taken from the outer rows of the four (4) row plots. The plants were pulled from the ground to include the root, and plant material above the flag leaf was discarded. Plant samples were placed in labeled Whirl-Pak® or Ziploc® bags and returned to the lab. Plant samples were washed to remove surface dirt, dried, and stored at room temperature.

Soil samples were processed to isolate colonies of *Phytophthora* spp. from field samples as follows. A one (1) gram dry soil sample was weighed. The one (1) gram sample was placed in a 48° C. molten 9 mL water agar test tube to a final volume of 10 mL. Water agar tubes were prepared dissolving 2.5 g Difco Bacto™ agar per liter of deionized water and 9 mL was added to individual test tubes. Water agar tubes were autoclaved and cooled until ready for use. The 1:10 water agar dilution soil sample was mixed with a Vortex-Genie™ until they were completely dissolved. A 1000 µL sample of the soil solution was then transferred to the surface of PAR media consisting of 17 g Difco corneal agar, 10 mg pimaricin, 10 mg rifampicin and 250 mg ampicillin and was adjusted up to a final volume of 1 liter with deionized water. The plates were incubated in the dark at 25° C. for two (2) days. After incubation, the soil-agar suspension was washed from the plate and *Phytophthora* colonies were identified and counted using low power microscopy.

The protocol to isolate *Phytophthora* spp. from host tissue was as follows: Root samples obtained from field plots were washed to remove surface dirt and air dried in aseptic labeled weigh boats. A two (2) to four (4) cm sample of root tissue was used from each plant sample. The dried samples were surface disinfected using a 5.25% NaOCl for one (1) to three (3) minutes. The plant sample was placed directly on PAR media amended with the following ingredients: 17 g autoclaved Difco Bacto™ cornmeal agar, 10 mg pimaricin, 10 mg rifampicin and 250 mg ampicillin. The solution was brought up to a final volume of one (1) liter with distilled water. Plates were poured to a volume of 25 mL media per Petri dish (100×15 mm). Plates with plant samples were incubated in the dark at 25° C. for two (2) days. Root segments were removed and samples were given a positive or negative rating depending on the identification of the fungus observed with high power microscope.

Soil samples were processed to isolate *Macrophomina phaseolina* colonies as follows: a 10 gram-soil sample was washed with 100 mL of 10% NaOCl solution in a Warring blender, and the sample was blended for three (3), five (5) second intervals over a two (2) minute period. The blended soil sample was passed through a No. 40-mesh (425 µm) sieve in tandem with a No. 325-mesh (45 µm) sieve and rinsed under running water for up to two (2) minutes. The sample was collected with a transfer pipette and transferred to a test tube. Sterile water was added for a final volume of 10 mL. Three (3) 100 µL samples were transferred to selective PDA-DORB media using a modified procedure described by Papavizas and Klag. The PDA-DORB was amended with the following ingredients per 500 mL media: 14.5 g Potato Dextrose Agar, 0.05 g Streptomycin sulfate, 0.0125 g Chlortetracycline hydrochloride, 0.025 g 4-dimethylamino-benzenediaosulfonic acid, 0.075 g rose bengal sodium salt, and 0.75 g bovine bile ox gall powder and distilled water up to the 500 mL final volume. Samples were incubated in the dark at 30° C. for seven (7) days. Colonies containing sclerotia were identified and counted using low power microscopy.

Plant samples were processed to isolate Macrophomina colonies as follows. Root samples taken at developmental stages R1, R4, and R6 were washed to remove dirt and root nodules and air dried for three (3) to five (5) days, the dried root samples were ground in a UDY Cyclone Mill® and collected in labeled plastic 150 mL bottles (UDY Corporation). A half strength stock solution of Potato Dextrose Agar, 14.5 g Difco Bacto™ dissolved in one (1) liter of distilled water and aliquotted in 100 mL's into 250 mL Wheaton bottles, 100 mL of molten PDA was added and autoclaved. Wheaton bottles were stored in a Precision® water bath at 55° C. until ready for use. After the PDA liquid cooled, 62.5 µL of Niaproof (Sodium 7-ethyl-2-methyl-4undecyl sulfate) was added to each Wheaton bottle. A 0.05 g ground plant sample was weighed and placed in a 50 mL beaker with 4 mL of 10% NaOCl and swirled to imbibe for approximately one (1) minute. After removing the Wheaton bottle from the water bath, it was placed in the sterile transfer hood and 500 µL of 5% streptomycin sulfate was added to PDA. The 5% streptomycin sulfate was prepared from stock solution by adding 5 grams of streptomycin sulfate to 100 mL sterile water and dissolved. One milliliter of 5% streptomycin sulfate was added to 1 mL sterile microfuge tubes and stored at 20° F. until needed. In the sterile transfer hood, the plant sample was washed into the amended PDA from the beaker with sterile water to insure the entire sample was placed in the PDA. The PDA was swirled to mix and approximately 25 mL per plate was poured into four (4) Petri dishes (100×15 mm) and then labeled. The plates were incubated in the dark at 30° C. for twelve (12) to fourteen (14) days. Plates were observed and given a positive or negative rating if fungal colonies containing sclerotia were present.

At the end of the growing seasons, marked by plant senescence, the two (2) interior yield rows were harvested using a Massey-Ferguson two-row experimental test, combined with an onboard computer processor for determining seed weight, seed moisture and collection of samples. Yield data included seed moisture and seed weight, which were used to determine the overall yield for each test plot.

Assessments were replicated over an initial two (2) year period: 1999 and 2000, as a foliar treatment, and a subsequent three (3) year period: 2003, 2004 and 2005. Identical field plots were planted at Kansas State University Extension Services in Columbus, Kans. and Parsons, Kans. All samples were obtained from the field site in Columbus and additional yield data was obtained from the Parsons, Kans. Field site.

FIGS. 1 and 3 depict the 1999 and 2000 Foliar Treatment Viability and Mortality Data. In 1999, the Carbenoxolone concentration was varied between 125 and 1000 µg/ml diluted in one gallon of water. The treatment composition was applied to the canopy of plants at various developmental stages (V-2, R-1 and R-6). The foliar application was accomplished using the pressurized boom-spray unit attached to a tractor at reproductive stage V-2 or R-1, or by a backpack spray unit at reproductive stage R-6. The mortality and viability data were collected at developmental stage R-8, usually around week eleven (11) or twelve (12) in the plant's lifecycle. Also shown in FIGS. 1 and 3, the percent mortalities were calculated based on the number of plants that died at twelve (12) weeks of growth as compared to the total number of seeds planted per treatment. The viability percentages as shown in FIGS. 1 and 3 were calculated from the total number of seeds planted per treatment, as compared to the viability data taken at three (3) weeks of growth. The seed germination rate was greater than 99% and was determined prior to planting. As can be seen in FIG. 1, foliar treatments utilizing 1000 µg/ml of Carbenoxolone had a mortality rate of approximately 20% and a viability rate of approximately 80%. This appears unchanged from the untreated control, which had similar percentages. However as can be seen, as the concentration of Carbenoxolone in solution is decreased, the mortality percentage decreases and the viability percentage increases when compared to the untreated control. The Carbenoxolone treatment solution having 125 µg/ml has a mortality percentage of approximately 10.4% compared to a mortality percentage of an uncontrolled of 20%. Similarly, the 125 µg/ml Carbenoxolone treatment solution increased the viability percentage approximately 10% from the uncontrolled treatment in 1999.

The 2002 foliar treatment using Cabenoxolone also had similar results as in 1999. The mortality percentage of plants treated with a Carbenoxolone solution decreased when compared to an untreated control. In 2000, Carbenoxolone treatments had a mortality percentage range of approximately 9% to approximately 17%, as compared to the untreated control, which had a mortality rate of approximately 24%. As can be expected with a decrease in mortality percentage, plants treated with Carbenoxolone had an increase in viability percentage as shown in FIG. 3.

FIG. 2 illustrates the 1999 Mean Disease Rating for Each Foliar Application, Percent Mortality and the Statistical Significance as Measured by the Student-Newman-Keuls ("SNK") Analysis. The disease ratings as shown in FIGS. 2 and 4 are an objective number rating assigned as a percentage of a plot infected having a rating scale of 1=0%, 2=25%, 3=50%, 4=75% and 5=100%. The SNK data comprising letters which are different are statistically significant from other letter assigned data sets, which allows the single year data to show how weather influences the outcome of the treatment. Also as shown in FIGS. 2 and 4, the percent mortality is the average number of dead plants divided by the average number of germinated plants per treated plot. The mortality count was taken at week eleven (11) in the 1999 and 2000 growing seasons. As previously stated, the SNK statistical analysis illustrate the statistical significance of the data, wherein means with the same letter are not statistically different. As can be seen from FIGS. 2 and 4, plants treated with the Carbenoxolone solution, whether 500 µg/ml or 1000 µg/ml, lowered the disease rating for the plants examined when compared to the control treatment. The Carbenoxolone treatment solution resulted in a disease rating of 1.7% whereas the control had a disease rating of 2.8%. Most significantly, the control had a 69% mortality rate whereas the 500 µg/ml Carbenoxolone solution had a 26% mortality rate. Even lower, 1000 µg/ml of Carbenoxolone solution a mortality rate of 22%.

Pre-emergence mortality data was obtained by totaling the number of seeds that failed to germinate. In the yield rows, two-hundred and forty (240) seeds were planted per row in the yield rows at the beginning of the growing season, flanked by two (2) rows (two-hundred and forty (240) seeds in each row) for plant sampling. Rows were end trimmed to final twenty-five (25) foot rows with two-hundred (200) seed per row and eight (8) seeds per foot. Mortality data was determined only from the interior yield rows. An average of these pre-emergence mortality totals, (four-hundred (400) seeds in two (2) rows) for all four (4) repetitions was taken to represent pre-emergence mortality. Pre-emergence mortality averages for each treatment with calculated standard deviations are compared in FIG. 5. Pre-emergence mortality indicates the number of plants that died before emergence. Treatments were either untreated control seed or seeds treated with the polymer in combination with Carbenoxolone. Foliar treatments indicate that the same compound used as a seed treatment was then applied as a foliar spray at a set plant development stage (R1 or R4). The percentage is based on the average of pre-emergence mortality compared to two-hundred and forty (240) seeds planted.

In 2003, the Carbenoxolone seed treatment showed the lowest number of pre-emergence mortality with an average of 26.25% non-emergent seeds, in comparison to untreated control groups which showed an average of 31.66% non-emergent seeds. Other treatments with high pre-emergence mortality averages include the polymer only, which showed an average of 37.08% non-emergent seeds. However, using the Student-Newman-Keuls Test for pre-emergence mortality data, no statistically significant difference was found between treatments. In 2004, Carbenoxolone displayed the lowest average pre-emergence mortality with an average of 43.33% non-emergent seeds, compared to the untreated control, with an average of 38.33% non-emergent seeds. Conversely, the polymer only, with an average of 41.66% non-emergent seeds, also showed higher averages of pre-emergence mortality in field conditions as compared to the untreated control. However, Student-Newman-Keuls Test for pre-emergence mortality showed no statistically significant differences between treatments. In 2005, the untreated control showed the lowest average pre-emergence mortality with an average of 23.75% non-emergent seeds. Carbenoxolone seed treatment had an average of 29.16% non-emergent seeds.

Foliar treatments consisted of untreated seed paired with a foliar treatment at developmental stages R1 and R4. Because foliar only treatments lacked seed treatments, these can be evaluated as internal controls within the field when compared to treated seed. These 2003 foliar only treatments, acting as non-treated seed controls ranged in pre-emergence mortalities from 27.50-35.41% compared to seed treatments which showed average percentages of 26.25-37.08%. In 2003, Carbenoxolone R1 foliar treatments showed a pre-emergence mortality with an average of 27.50% non-emergent seeds, while Carbenoxolone R4 foliar showed an average of 35.41% non-emergent seed. The 2004 foliar only treatments showed pre-emergence mortality percentages ranging form 32.50-40.83% for non-treated seed controls compared to seed treatments which showed average percentages of 37.08-43.33%. Foliar R1 Carbenoxolone treatment alone also showed a pre-emergence mortality average of 41.25% non-emergent seeds. Foliar R4 Carbenoxolone showed the highest pre-emergence mortality rate with an average of 43.75% non-emergent plants. In 2005 non-treated seed and foliar only controls showed averages pre-emergence mortality percentages ranging from 27.08-31.25%, compared to seed treatments which showed averages ranging from 28.33-30.0%. Carbenoxolone R1 foliar treatment showed the lowest average of pre-emergence mortality of any of the treatments with only 27.08% non-emergent seeds. Carbenoxolone R4 foliar treatment showed an average of 27.91% non-emergent seeds.

In 2003, Carbenoxolone seed combined with an R1 foliar treatment showed the lowest rate of pre-emergence mortality of any combination treatment with an average of 30.0% non-emergent seeds. Carbenoxolone seed with an R4 foliar showed an average of 36.66% non-emergent seeds. In 2004, Carbenoxolone seed in combination with R1 foliar application showed an average of 41.24% non-emergent seeds, indicating a lower pre-emergence mortality. Carbenoxolone seed treatments in combination with a R4 foliar application showed the highest rates of pre-emergence mortality of all treatments having 42.5%, pre-emergence mortality percentage. In 2005, Carbenoxolone seed and R4 foliar treatment showed a relatively low average pre-emergence mortality rate of 28.75% non-emergent seeds. Carbenoxolone seed with R1 foliar treatments showed an average of 30.0% non-emergent seeds.

Post-emergence mortality was obtained by totaling the number of dead plants at the end of the growing season as compared to the number of plants that successfully emerged. Plant mortality counts were taken at developmental stage R8, within the two (2) yield rows and an average of these mortality totals was obtained for all four (4) repetitions. Post-emergence mortality averages and standard deviations for all four (4) repetitions and treatments over three (3) years of testing are compared in FIG. 6. Post-emergence mortality indicates the number of plants that died within the growing season after emergence. Similar to FIG. 5, treatments were either untreated control seed or seeds treated with the polymer in combination with Carbenoxolone. Foliar treatments indicate that the same compound used as a seed treatment was then applied as a foliar spray at a set plant development stage (R1 or R4). The percentage is based on the average of V1 emerged viable seedlings counted compared to the R8 viable plants counted.

In 2003, treatments that showed higher numbers of post-emergence mortality included Carbenoxolone seed with an average of 5.0%. This is compared to untreated control with an average of 3.75%, and the polymer control which had an average of 4.58%. In 2004, data showed Carbenoxolone seed displayed higher post-emergence mortality average of 2.08% during the growing season, compared to the untreated control which had an average of 1.25%. Other treatments that showed a slightly reduced mortality average included, the polymer with an average of 1.25% during the growing season. In 2005, treatments that showed lower plant post-emergence mortality averages were untreated control and Carbenoxolone seed treatment; both with an average of 2.5%. The polymer treatments showed slightly higher average post-emergence mortality rates with an average of 4.16%.

In 2003, Carbenoxolone R4 foliar treatment displayed an average of 6.25%, and Carbenoxolone R1 treatment had an average of 5.0%. In 2004, Carbenoxolone R1 and R4 foliar treatments both showed an average of 1.6%. In 2005, the treatments Carbenoxolone R1 foliar and Carbenoxolone R4 foliar displayed 3.33% average.

In 2003, Carbenoxolone seed in combination with an R4 foliar treatment showed an average of 2.9% post-emergence mortality, the lowest number of the growing season. Carbenoxolone seed with an R1 foliar treatment displayed a higher average of 5.41% during the post-emergent growing season. In 2004, combination treatments Carbenoxolone seed with an R1 foliar showed the lowest post-emergence mortality average with only 1.25% plant deaths during the post-emergent growing season. Carbenoxolone seed with an R4 foliar displayed a slightly higher average of 2.08% during the post-emergent growing season. In 2005, Carbenoxolone seed with an R4 foliar combination treatment showed the lowest average with only 2.5% during the growing season. Carbenoxolone seed with an R1 foliar treatment displayed a post-emergence average of 3.33% during the growing season.

The viability data was obtained by totaling the number of healthy plants within the two (2) yield rows at the end of the growing season when plants reached developmental stage R8 and these totals were averaged and standard deviations calculated for all four (4) repetitions per treatment. Viability averages indicate the number of healthy plants at the end of the growing season taking into account the number of plants that failed to germinate (pre-emergence mortality) and those that died during the growing season (post-emergent mortality). Viability averages of all treatment repetitions for a growing year, for three (3) years of field-testing are compared in FIG. 7. Viability indicates the number of healthy plants at the end of the growing season. Similar to FIGS. 5 and 6, treatments were either untreated control seed or seeds treated with the polymer in combination with Carbenoxolone. Foliar treatments indicate that the same compound used as a seed treatment was then applied as a foliar spray at a set plant development stage (R1 or R4). Percentage is based on the average number of viable plants counted at R8.

In 2003, viability data indicated a difference in germination frequency and viability of seed. Although Student-Newman-Keuls showed no statistically significant differences between the treatments tested, the majority of Carbenoxolone seed treatments showed increasing trends toward improving plant viability compared to most of the untreated and polymer only controls. Carbenoxolone seed treatments showed a mean viability average of 78.39% at the end of the growing season. Untreated control plots showed an average of 72.91% and the polymer only control showed an average of 67.91%. In 2004, the polymer only had an average of 62.91% followed Carbenoxolone seed with a viability average of 61.66%. However Student-Newman-Keuls Test for viability in 2004 indicated no statistically significant differences in plant viability between any treatments tested. In 2005, the untreated control group showed the highest overall viability average of 80.83%. The polymer showed an average of 76.25%, while Carbenoxolone seed treatment displayed an average of 75.41%. Student-Newman-Keuls Test revealed no statistically significant differences between plant viability due to any of the treatments compared in 2005.

In 2003, Carbenoxolone R1 foliar treatment had the highest viability average of 77.08% at the end of the growing season. Carbenoxolone R4 foliar showed a slightly lower viability average with 69.16%. In 2004, Carbenoxolone R1 foliar showed an average of 63.33% while Carbenoxolone R4 foliar had an average of 60.83%. In 2005, Carbenoxolone R1 foliar showed the highest viability average of 77.5%. Carbenoxolone R4 foliar had a viability average of 76.66%.

In the 2003-growing season, Carbenoxolone seed with an R1 foliar treatment showed the highest viability with an average of 74.58%. Carbenoxolone seed combined with an R4 foliar displayed a viability average of 69.58%. In 2004, Carbenoxolone seed combined with an R4 foliar treatment showed a viability average of 62.08%. Carbenoxolone seed combined with an R1 foliar showed an average of 63.75%. In 2005, Carbenoxolone seed treatments combined with an R4 foliar treatment had a viability average of 75.83% at the end of the growing season. Carbenoxolone seed combined with an R1 foliar treatment had an overall viability average of 74.58%. Dunnett's t Test analysis of viability data indicated a statistically significant difference between Carbenoxolone seed combined with an R1 foliar treatment compared to the untreated control.

Statistical analysis was also conducted for each specific year's propagule numbers (FIG. 8). In 2003, Student-Newman-Keuls and Dunnett's t Test revealed that no specific statistical difference existed for treatments at plant developmental stages V1, R1 and R4 in relation to the amount of *M. phaseolina* and *Phytophthora* propagule present. In 2004, Student-Newman-Keuls Test and Dunnett's t Test revealed no statistically significant differences between treatments at development stages V1 or R1 in relation to the amount of *M. phaseolina* and *Phytophthora* propagules present. In 2005, Student-Newman-Keuls and Dunnett's t Test revealed that no statistically significant differences existed between treatment at development stages V1, R1 and R4, in regard to amount of *M. phaseolina* and *Phytophthora* propagules present. In FIG. 13, mean indicates average number of enumerated colonies for years 2003, 2004 and 2005 and SNK groupings with different letters are significantly different within treatment. Multiple comparisons were tested at $\alpha=0.1$. As with previous Figures, treatments were either untreated control seed or seeds treated with the polymer in combination with Carbenoxolone. Foliar treatments indicate that the same compound used as a seed treatment was then applied as a foliar spray at a set plant development stage (R1 or R4).

Yield data was obtained from the two (2) yield rows of twenty-five (25) feet using a conversion equation which utilized the fraction of acreage predetermined test weight and adjusted moisture of the seeds harvested. Yield values represent bushels per acre adjusted for moisture and test weight. Yield data indicated no statistically significant differences between 2003, 2004 and 2005. Yield averages for all three (3) years are shown in FIG. 9. In FIG. 9, mean indicates average number of enumerated colonies for years 2003, 2004 and 2005, and SNK groupings with different letters are significantly different within treatment. Multiple comparisons were tested at $\alpha=0.1$. Again as with previous Figures, treatments were either untreated control seed or seeds treated with a seed coating polymer in combination with Carbenoxolone. Foliar treatments indicate that the same compound used as a seed treatment was then applied as a foliar spray at a set plant development stage (R1 or R4).

It has been shown that soybeans are under constant pressure from disease and subsequent environmental factors during the growing season. Due to the range of challenges in growing healthy plants, there is a constant need for development of control methods to deter plant pathogens and assist plants in healthy growth and development. The methods and compositions disclosed herein for fungal disease management were employed as seed only treatments, foliar only and combination seed and foliar treatments applied to foliage at specific reproductive stages to assess possible management of fungal disease. Control treatments were used to compare effectiveness of these compositions in relation to early and mid-season diseases causing *Pythium*, *Phomopsis*, *Rhizoctonia*, and *Phytophthora*. Although the methods disclosed herein concentrated on elucidating the effects of these novel compositions on *Phytophthora* and *Macrophomina phaseolina* infection and colonization, the methods and compositions disclosed herein may be used to treat other fungal disease, including but not limited to, *Acremonium* spp., *Alternaria* spp., *Arkoola nigra*, *Cercospora kikuchii*, *Cercospora sojina*, *Choanephora infundibulifera*, *Choanephora trispora*, *Colletotrichum dematium f. truncatum*, *Colletotrichum truncatum*, *Corynespora cassiicola*, *Cylindrocladium crotalarie*, *Dactuliochaeta glycines*, *Diaporthe phaseolorum*, *Diaporthe phaseolorum* var. *caulivora*, *Drechslera glycines*, *Fusarium solani f.* sp. *glycines*, *Glomerella glycines*, *Leptosphaerulina trifolii*, *Meocosmospora vasinfecta*, *Microsphaera diffusa*, *Mycoleptodiscus terrestris*, *Peronospora manshurica*, *Phakopsora pachyrhizi*, *Philophora gregata*, *Phoma* spp., *Phomopsis* spp., *Phyllosticta sojaecola*, *Phymatotrichopsis omnivora*, *Pyrenochaeta glycines*, *Pythium* spp., *Rhizoctonia* spp., *Sclerotium rolfsii*, *Sclerotinia sclerotiorum*, *Septoria glycines*, *Spaceloma glycines*, *Stemphylium botryosum*, and *Thielaviopsis basicola*. Further, *Phytophthora* spp. may be *Phytophthora sojae*. The fungal disease *Pythium* spp. may be *Pythium aphanidermatum*, *Pythium debaryanum*, *Pythium irregulare*, *Pythium myriotylum* or *Pythium ultimum*. The fungal disease *Rhizoctonia* spp. may be *Rhizoctonia solani*. Furthermore, in addition to seed only treatments, foliar only treatments and combination seed and foliar treatments, the compositions may be applied to a tuber of the plant, may be applied to a portion of the roots of the plant or may be applied to the soil surround the plant or seed.

The primary role of a seed treatment is to improve seed germination and protect emerging plants. A plant treated using the methods of applying the compositions disclosed herein provide a level of protection against diseases, such as those caused by *Phytophthora, Pythium, Rhizoctonia*, and *Phomopsis*. However, in the presence of high soil moisture, the protective levels are reduced possibly due to the water-soluble property of the treatment allowing the active agents to be washed from the developing rhizosphere. Thus, these novel methods and compositions may be combined with a polymer coating reducing or eliminating the treatments from being washed from the seed coat. The compositions including the polymer coating increases their effectiveness in soil and decreases the incidence of disease infection. The composition of Carbenoxolone and the polymer (Magnacoat®) showed significant improvements over the control treatments. During drought stress, foliar applications at reproductive stage R1 benefited the plant in the presence of mid-season diseases such as *M. phaseolina*; however, when drought stress was not as prominent, application of foliar treatments at reproductive stage R4 was a benefit to the plant.

Yield was improved with Carbenoxolone composition seed treatment combined with an R1 foliar treatment. An increase of 1.5 bushels per acre was observed, this was a 6.9% increase compared to other treatments over the three years of testing. This general yield tread displays the importance of healthy plants during the growing season, which ultimately determines the overall yield for a season.

The foregoing field study results indicate that during the early and late seasons each growing season, weather had a significant impact on disease pressure and how well the treatments performed well. In general, during the 2003, 2004, and 2005 growing seasons, there was less drought pressure which greatly reduced the occurrence of Charcoal rot symptoms and disease in the three (3) years of this test. In addition, planting time, spring temperatures, the occurrence and amount of rain post-planting and at critical plant developmental stages also impact diseases such as *Phytophthora Phomopsis, Pythium*, and *Rhizoctonia*.

Rainfall amounts, timing, and temperature impact several important factors in plant disease development. First, early season rainfall, soon after planting, can compress the soil making it difficult or impossible for seedlings to emerge from the soil. Secondly, the availability of water, coupled with cool temperatures can facilitate certain pathogens (*Phytophthora* and *Pythium*) to germinate and move to the host plant. Additionally, heavy rain can stress the plant as well, creating hypoxic conditions in the soil and the rhizosphere which contributes to root rot or blight favorable conditions, but also decreasing over-wintering sclerotia of Macrophomina phaseolina. Later in the season, as the plant begins its reproductive stages of growth, rainfall is again critical due to the stress of flowering and the typical July and August drought conditions found in Southeast Kansas. If rainfall occurs at this critical R1 plant developmental stage, and rain keeps soil moisture adequate for normal plant development, very little Charcoal rot or mid-season plant disease occurs. An additional factor affected by rainfall when field-testing seed treatments is the solubility of the treatments themselves. Variations in germination indicate that water-soluble seed treatments are affected by the presence of higher rainfall averages before and after planting. The polymer coating used herein, Magnacoat®, is a polyether resin, which may be flowable in water. In addition, Carbenoxolone is water-soluble which enhances the probability that the treatment will be washed off the seeds in heavy rainfall or wet soil conditions found in the spring. There is highly variable spring weather for each growing season of 2003, 2004, and 2005. In 2003, weather data for Columbus, Kans. indicated a high of 71° F. and a low of 49° F. on the day of planting, a range of 22° for that day. In 2004, temperatures during planting were a of high 86° F. and low 60° F., with a range of 26°, for that day. In 2005, at time of planting, temperatures were recorded at a high of 88° F. and a low of 65° F., a 23° difference for that day.

Pre-emergence mortality could possibly be caused by many factors, such as heavy rains after planting, damaged seed due to treatment method or seed infected before planting. In this study, damaged seed was taken into account and attempts were made to reduce the incidence of planting damaged seed. Weather/rainfall data did help explain how environmental stress probably played a part in disease development in each year of the test. In 2005, reduced early season rainfall showed lower pre-emergence mortality rates. This is evident in control treatments when 2005 is compared to 2004, there is a significant reduction in early season death in 2005. Untreated control pre-germination mortality in 2005 compared to 2004 was reduced from 38% to 23%, and polymer treated seed mortality was reduced from 41% to 28%. Saturated soil is preferential to the development of early season diseases such as *Phytophthora* rot of soybeans as well as, *Pythium, Phomopsis* and *Rhizoctonia*. Due to reduced rainfall the pressure of early season disease was reduced somewhat. As seen in FIG. 1, pre-emergence mortality for untreated control was 31% in 2003, compared to 38% in 2004, and 23% in 2005.

The polymer treatment showed difference in pre-emergence mortality of 37% in 2003, 41% in 2004 and 28% in 2005. From the corresponding weather data the increase in rainfall had a significant affect on the polymer's solubility and impacted the amount of early disease pressure. In 2004 compared to 2003, germination was reduce by 4% and in 2004 compared to 2005 germination was reduced by 13%. The Carbenoxolone seed treatment only showed differences in pre-emergence mortality of 26% in 2003 compared to 43% in 2004 and 29% in 2005. This suggests that an increase in rainfall affected the germination pattern and viability of seeds treated with Carbenoxolone with the polymer. In 2003, average germination of Carbenoxolone seed treatments was 17% higher compared to 2004. In 2004, however there was an increase in rainfall by 1.62 inches in the month of July. The possibility of the active ingredients being washed from the seed in 2004 is one possible explanation for the higher disease incidence during that testing year. Because rainfall totals of 2004 were comparable to 2005, it is speculated that rainfall is involved in the low germination of treated seed, most likely due to increased early disease pressure favored by soil moisture due to higher rainfall before planting.

In analyzing the data, chemical seed treatment controls enabled specific disease pressures to be determined due to the specific target pathogens they inhibit. The 2003 planting season had the lowest rainfall totals for the month of June, reducing pre-emergence mortality average ranging from 25-36%. In the 2004 growing season, higher rainfall was considered optimal for early season diseases and resulted in higher pre-emergence mortality averages. In pre-emergence mortality, the 2004 growing season was shown to have the highest mortality averages ranging from 39-43%. This mortality data is in good agreement with that found in high disease pressure conditions favored by high moisture content and low spring temperatures. In addition, 2005 pre-emergence mortality averages ranged from 23-30%. There were no statistically significant differences in inoculum load of *Phytophthora* spp. in soil between all three testing years. This suggests that there was some consistent early disease pressure on the treatment for all years tested.

A comparison of rainfall data indicates that there are ideal conditions for seed germination and plant vigor compared to the development of disease. Rainfall averages in 2005 indicate ideal conditions for plants; however rainfall was intermediate in 2005 compared to 2003 and 2004, which could mean that drier conditions later in the plants life put additional stress on the plants. Drier conditions might not be as favorable for specific early disease development, but other factors could have an affect on the plants health, such as ability to emerge from dry compacted soil or possibly lack of moisture affecting germination patterns or absorbency factors of the seed coat.

Charcoal rot development was most common during times of drought stress coupled with reproductive stages in plants when this additional stress is added to the plants. The post-emergence mortality average was highest in 2003 indicating that drought stress greatly affected overall plant health and the occurrence of mid-season diseases such as Charcoal rot. In 2003, R4 foliar treatments displayed some protective qualities during the drought that year. There was no improvement in plants that received these same foliar treatments at R1 plant developmental stage. It has been shown that plants are under added stress during reproductive stages, such as R4, when pod set occurs, and this added physiological vulnerability can decrease the plant's defenses making it more susceptible for disease development.

As shown in FIG. 2, Carbenoxolone seed combined with an R1 foliar treatment showed an average of 5% post-emergence mortality compared to Carbenoxolone seed combined with an R4 foliar treatment which showed an average of 2% post-emergence mortality. The only treatment that did not display this trend was Carbenoxolone foliar R1 or R4 treatments. It was shown in the post-emergence data that seed treatments showed little mid to late season protection in 2003. In 2003, plots with seed treatments displayed higher post-mortality averages than those with foliar treatments. From post-emergence mortality data and rainfall conditions it is speculated that moderate rainfall before reproduction is of more benefit than heavier rainfall during or after reproduction. This was displayed in higher post-emergence mortality data of 2003 compared to 2004. Sufficient rainfall before reproduction has a major impact on early season health of the plant which then could be affected by other environmental variables later in the season. Variables such as mid-season disease pressures and drought stress which take a significant toll on plant health.

In 2004, Carbenoxolone R1 foliar, Carbenoxolone R4 foliar treatment and Carbenoxolone seed combined with an R1 foliar treatment showed the lowest incidence of post-emergence mortality all with averages of 1.6%. In 2004, R1 foliar treatments seem to be more effective against late season disease pressure. This could be attributed to soluble properties of active compounds and the presence of rain after application or the level of protection differs in specific environmental conditions. However, seed treatments alone showed the same trend of post-emergence mortality indicating that weather has a significant impact on plant health, regardless of the treatment employed. This indicated that during the 2004 growing season, less overall post-emergent disease occurred and is consistent with rainfall and availability of moisture throughout the growing season.

In 2005, post-emergence mortality averages fell between those found in 2003 and 2004. Post-emergence mortality averages were consistent for all treatments. Low averages included Carbenoxolone seed with an R4 foliar treatment having an average of 2% post-emergence mortality. All other foliar and combination seed and foliar treatments showed averages of 3.33-3.74% post-emergence mortality and these include: Carbenoxolone R1 foliar treatment, Carbenoxolone R4 foliar and Carbenoxolone seed combined with an R1 foliar treatment at 3.33% post-emergence mortality. This indicates that conditions in 2005 were fairly good since there was consistent rainfall and available moisture throughout the growing season.

As shown in FIG. 3, viability data for 2003 indicated that mid-season drought stress had a significant affect on post-emergence viability. However, due to a reduction in pre-emergence mortality that year, the overall viability values were somewhat consistent with those of 2005. For untreated control treatments, average viability was 8% less in 2003 than in 2005. The polymer only treatment had a viability average of 9% less in 2003 compared with 2005. Interestingly, not all treatments showed this trend, such as a Carbenoxolone seed treatment, Carbenoxolone seed combined with an R1 foliar treatment, Carbenoxolone R1 foliar treatment and commercial seed treatments, which all showed few viability difference between years.

In 2003, average viability percentages ranged from 67-78% viability. However, in 2004 average viability percentages were significantly reduced, averages of 60-65%. In 2005, viability data indicated a significant reduction in overall viability percentages ranging from 74-80% for all treatments examined. These variations were most likely due to early season soil saturation which would favor soil-borne disease development in emerging plants. For 2003, 2004, and 2005, germination and emergence seemed to be the critical factor in overall plant viability percentages. Because of the water-soluble properties of specific seed treatments, residual protection was most likely reduced when the seedlings were exposed to heavy rainfall during emergence. Viability and rainfall data indicate that in dryer conditions seed treatments provide some residual protection in the presence of fungal disease, but if the soil is saturated immediately after planting, less seed protective qualities were apparent and emergence could be critically reduced. In addition, for 2003, 2004, and 2005, very little drought stress mid to late season occurred and thus few Charcoal rot diseases symptoms were present. It appears that during these three years of testing that early season pre-emergence disease problems were predominant.

Yield data indicates that although no specific treatment statistically increased the amount of yield, Carbenoxolone did consistently improve the average yield by approximately 1.5 bushels/acre. It should be noted that placement of repetitions in the field did have an effect on the bushels per acre recorded for all three years. The field site in Columbus, Kans. displays a clay pan and reduced topsoil in specific areas of the field. Due to the reduction of topsoil and its subsequent absorptive properties, the trend for increased soil saturation due to the clay layers water holding capacity and the reduced moisture availability during drought conditions the site displayed statistically significant reduction in yield in specific repetitions.

What is claimed is:

1. A method of protecting a soybean plant from a soil-borne fungal disease, comprising the steps of:
    applying to at least a portion of said soybean plant an amount of a composition to reduce or prevent the occurrence of *Phytophthora* spp. or *Pythium* spp. in said soybean plant, wherein said composition includes carbenoxolone disodium salt and a polymer.

2. The method of claim 1 wherein said polymer is water-insoluble, water-soluble or flowable.

3. The method of claim 1 wherein said step of applying said composition comprises the step of applying said composition to said plant as a foliar spray.

4. The method of claim 1 wherein said composition is in an aqueous solution.

5. The method of claim 1 wherein said *Phytophthora* spp. is *Phytophthora sojae*.

6. The method of claim 1 wherein said *Pythium* spp. is selected from the group consisting of *Pythium aphanidermaturn, Pythium debaryanum, Pythium irregulare, Pythium myriotylum* and *Pythium ultimum*.

7. The method of claim 1 wherein said polymer is a polyether resin.

8. A method of protecting a soybean seed from a soil-borne fungal disease, comprising the steps of:
    applying a composition comprising Carbenoxolone disodium salt and a polymer to at least a portion of said soybean seed to reduce the occurrence of *Phytophthora* spp. or *Pythium* spp.

9. The method of claim 8 wherein said polymer is water-insoluble, water-soluble or flowable.

10. The method of claim 8 wherein said step of applying said composition comprises applying said composition to said plant as a foliar spray.

11. The method of claim 8 wherein said polymer is a polyether resin.

12. The method of claim 8 wherein said *Phytophthora* spp. is *Phytophthora sojae*.

13. The method of claim 8 wherein said *Pythium* spp. is selected from the group consisting of *Pythium aphanidermatum, Pythium debaryanum, Pythium irregulare, Pythium myriotylum* and *Pythium ultimum*.

14. A method of protecting a soybean plant or reducing mortality of a soybean seed from a soil-borne fungal disease, comprising the steps of:
    applying an amount of a composition comprising carbenoxolone disodium salt and a polymer to at least a portion of said soybean plant as a foliar spray to reduce the occurrence of *Phytophthora* spp. or *Pythium* spp.

15. The method of claim 14 wherein said polymer is water-insoluble, water-soluble or flowable.

16. The method of claim 14 wherein said composition is in an aqueous solution.

17. The method of claim 14 wherein said *Phytophthora* spp. is *Phytophthora sojae* and said *Pythium* spp. is selected from the group consisting of *Pythium aphanidermatum, Pythium debaryanum, Pythium irregulare, Pythium myriotylum* and *Pythium ultimum*.

* * * * *